United States Patent [19]

Flom et al.

[11] Patent Number: 5,817,062

[45] Date of Patent: Oct. 6, 1998

[54] TROCAR

[75] Inventors: James R. Flom, Palo Alto; Pinaki Ray, Redwood City, both of Calif.

[73] Assignee: Heartport, Inc., Redwood City, Calif.

[21] Appl. No.: 672,164

[22] Filed: Jun. 27, 1996

Related U.S. Application Data

[63] Continuation-in-part of Ser. No. 615,151, Mar. 12, 1996.

[51] Int. Cl.⁶ ........................................ A61M 5/32
[52] U.S. Cl. .......................... 604/174; 604/164; 604/104
[58] Field of Search ..................... 604/104, 105, 604/106, 107, 108, 109, 174, 175, 178

[56] References Cited

U.S. PATENT DOCUMENTS

| | | |
|---|---|---|
| 1,719,428 | 7/1929 | Friedman . |
| 1,828,986 | 10/1931 | Stevens . |
| 1,863,057 | 6/1932 | Innes . |
| 1,870,942 | 8/1932 | Beatty . |
| 2,556,783 | 6/1951 | Wallace . |
| 3,108,595 | 10/1963 | Overment . |
| 3,397,699 | 8/1968 | Kohl . |
| 3,692,029 | 9/1972 | Adair . |
| 3,713,447 | 1/1973 | Adair . |
| 3,717,151 | 2/1973 | Collett ..................................... 604/106 |
| 3,915,171 | 10/1975 | Shermeta . |
| 3,938,530 | 2/1976 | Santomieri . |
| 3,946,741 | 3/1976 | Adair . |
| 4,535,773 | 8/1985 | Yoon . |
| 4,617,929 | 10/1986 | Gill . |
| 4,655,752 | 4/1987 | Honkanen et al. . |
| 4,716,901 | 1/1988 | Jackson et al. . |
| 4,944,732 | 7/1990 | Russo ..................................... 604/247 |
| 4,995,868 | 2/1991 | Brazier ................................... 604/105 |
| 5,007,900 | 4/1991 | Picha et al. . |

(List continued on next page.)

FOREIGN PATENT DOCUMENTS

| | | |
|---|---|---|
| WO 93/20741 | 10/1993 | WIPO . |
| WO 94/00059 | 1/1994 | WIPO . |
| WO 94/20025 | 9/1994 | WIPO . |

OTHER PUBLICATIONS

Surgi–Tech Advanced Thoracoscopic Instruments.
Origin Medsystems, Inc., Thoracic Trocar and Sleeve instructions for use, Single Use Surgical Trocar—Thoracic, PN01065 Rev. A.
Stapleoscopy Products brochure, pp. 10–11, no date.
Ethicon Endo–Surgery, Endoscopic Products, Trocars & Accessories, Endopath Specialty Trocars, Single Patient Use, p. B5, no date.
Snowden–Pencer, Product Profile, Reusable Thora–Port, product advertisement© 1993.
Pilling Weck, Ecosystem Endoscopic Entry Devices product brochure, no date.
"Vendor Round Table," *Surgical Products,* Nov., 1994, pp. 14–15.
Marlow Surgical Technologies, Inc., Hasson SAC Stable Access Cannula, product advertisement, no date.
Threaded Fascia Holders and Trocars, p. 22, Trocar Sleeve Anchor, Chest Port, Pyramidal, Conical, no date.
Olympus, "The Olympus Thoracofiberscope Offers Maximum Visualization for Diagnosis and Treatment," product advertisement, R70E–0992B, no date.
Cook, Procar, p. 19, product catalog, no date.

(List continued on next page.)

*Primary Examiner*—Sam Rimell
*Assistant Examiner*—Luke J. Yeh
*Attorney, Agent, or Firm*—Jeffry J. Grainger; Jens E. Hoekendijk; Michael J. Lynch

[57] ABSTRACT

A thoracic trocar having a deflectable member. The deflectable member has a frustoconical outer surface and is movable between first and second positions. The outer surface is angled toward the distal end in the first position and angled toward the proximal end in the second position. The first and second positions are both stable, unbiased positions and the deflectable member is movable from the first position to the second position upon application of the necessary force.

13 Claims, 11 Drawing Sheets

U.S. PATENT DOCUMENTS

| | | | |
|---|---|---|---|
| 5,122,114 | 6/1992 | Miller | 604/49 |
| 5,122,122 | 6/1992 | Allgood | 604/174 |
| 5,147,316 | 9/1992 | Castillenti . | |
| 5,152,754 | 10/1992 | Plyley et al. . | |
| 5,176,649 | 1/1993 | Wakabayashi . | |
| 5,201,742 | 4/1993 | Hasson . | |
| 5,203,773 | 4/1993 | Green | 604/104 |
| 5,209,741 | 5/1993 | Spaeth . | |
| 5,217,441 | 6/1993 | Shichman . | |
| 5,217,451 | 6/1993 | Freitas | 604/105 |
| 5,221,281 | 6/1993 | Klicek . | |
| 5,224,951 | 7/1993 | Freitas . | |
| 5,234,447 | 8/1993 | Kaster et al. . | |
| 5,242,409 | 9/1993 | Buelna . | |
| 5,246,424 | 9/1993 | Wilk . | |
| 5,248,302 | 9/1993 | Patrick | 604/105 |
| 5,256,147 | 10/1993 | Vidal et al. . | |
| 5,256,149 | 10/1993 | Banik et al. . | |
| 5,257,973 | 11/1993 | Villasuso . | |
| 5,279,567 | 1/1994 | Ciaglia et al. . | |
| 5,284,474 | 2/1994 | Adair . | |
| 5,290,249 | 3/1994 | Foster et al. | 604/174 |
| 5,300,036 | 4/1994 | Muller et al. . | |
| 5,324,268 | 6/1994 | Yoon . | |
| 5,336,206 | 8/1994 | Shichman . | |
| 5,338,305 | 8/1994 | Plyley et al. . | |
| 5,350,393 | 9/1994 | Yoon . | |
| 5,352,206 | 10/1994 | Cushieri et al. . | |
| 5,354,283 | 10/1994 | Bark et al. . | |
| 5,356,421 | 10/1994 | Castro . | |
| 5,366,445 | 11/1994 | Haber et al. . | |
| 5,368,607 | 11/1994 | Freitas . | |
| 5,370,625 | 12/1994 | Shichman . | |
| 5,391,156 | 2/1995 | Hildwein et al. . | |

OTHER PUBLICATIONS

Specialty Surgical Instruments, Ultra Endo–Vasive Instrumentation, Open Laparoscopy Sleeves, p. 15, no date.

Specialty Surgical Instruments, Apple Medical, p. 21, Lehrer Open Laparascopy Cannula, 12mm Secondary Cannula with Trocar, no date.

Herzog Surgical, Inc., Entree, Thoracoscopy Trocar and Cannula, product catalog, no date.

Herzog Surgical, "JARIT, Endocscopic Instrumentation," product brochure, pp. 22–23, Canula and Trocar, Trocar, Cannula and Trocar, Flexible, Hasson Cannula, Reducer Sleeve, Dilation Set, Veress Needle, no date.

Arthrex, Femoral Pin Placement, pp.1,4, Transtibial Femoral Guide, Tibial Tunnel Guide, Arthrex Sheathed Interference Screws, Arthrex Non–Sheathed Cannulated Interference Screws, no date.

Snowden–Pencer, Fine Instruments for Endoscopic Surgery, product brochure, p. 13, no date.

Arthrex, Inc., *The Complete Arthrex Information System*, Product Catalog, Arthroscopic Surgery Basic Instrumentation and Equipment, pp. 5,9, no date.

Cabot medical, Trocan: A more cost–effective approach in disposable trocar and cannula, product advertisement, ©Mar. 1991.

Way, Lawrence, W., Advances in Intraluminally Laparascopy, Laparascopic Pancreatic Cystgastrostomy using R.E.D. (Radially Expanding Dilator), vol. 1, No. 1, 1993, *InnerDyne Medical, Inc.*

Daniell, James, "Advances in Laparascopy, Laparascopic Treatment of Endometriosis using the Radially Expanding Dilator,"*InnerDyne Medical, Inc.*, vol. 2, No. 1.

InnerDyne Medical, R.E.D. Radially Expanding Dilator, Instructions for Use, 610–06–0019L, no date.

InnerDyne Medical, R.E.D. Radially Expanding Dilator, ©1993.

InnerDyne Medical, "Expanded Access System for Intraluminal Endoscopy," product description , no date.

Cook Surgical, *Cook Thoracoscop Introducers,* C–Port393, ©1993.

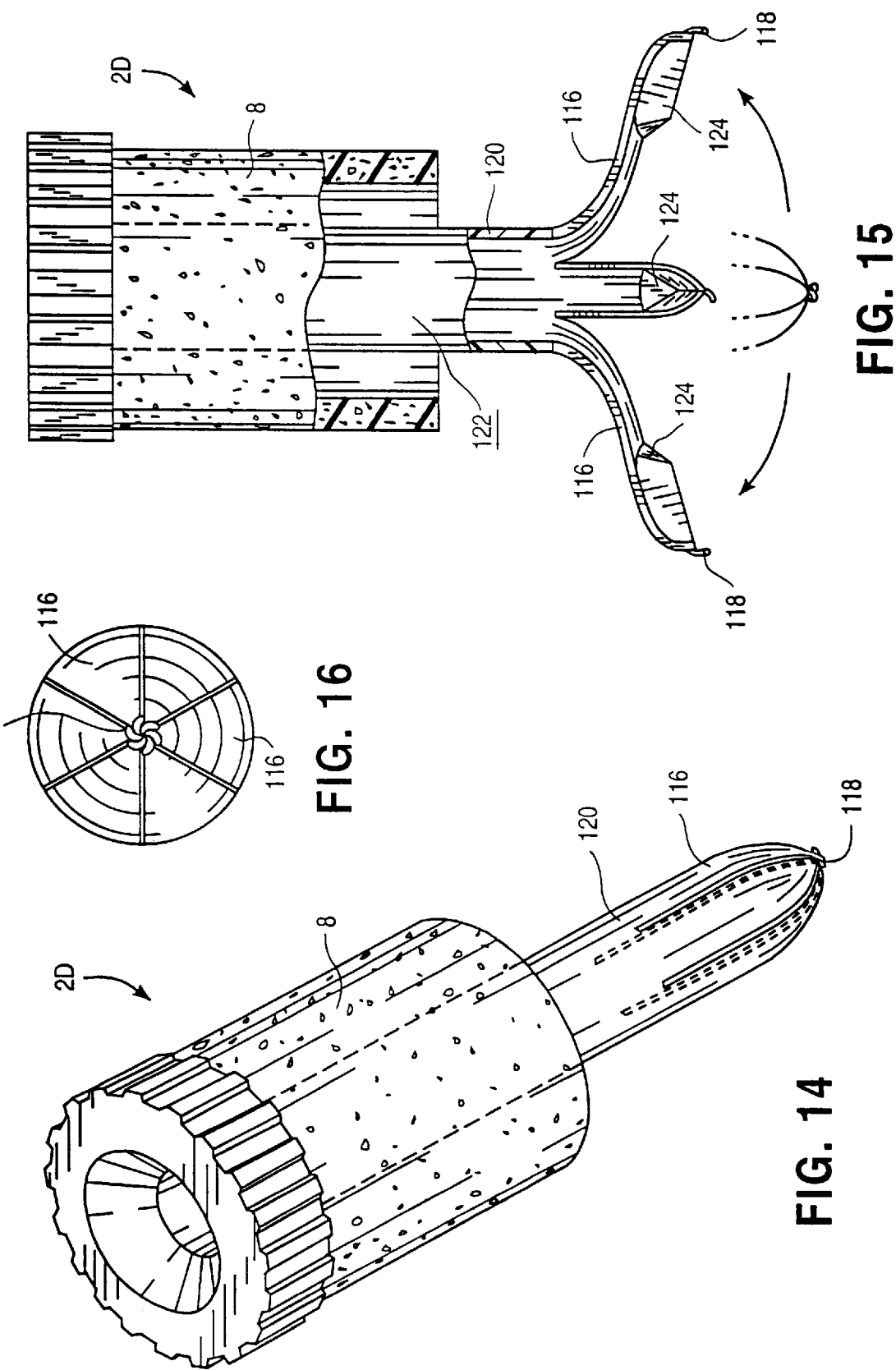

TROCAR

CROSS-REFERENCE TO RELATED APPLICATION

The present application is a continuation-in-part of U.S. patent application Ser. No. 08/615,151 filed Mar. 12, 1996.

FIELD OF THE INVENTION

The present invention relates to trocars and their methods of use. A specific application of the trocar is developed with respect to use in a patient's thoracic cavity, however, the trocars may be used for any other purpose. The trocars provide a path for surgical instruments into a patient.

BACKGROUND OF THE INVENTION

Trocars are generally used as access devices for introduction of other surgical instruments into a patient. A conventional thoracic trocar is disclosed in U.S. Pat. No. 5,279,575 to Sugarbaker. In U.S. Pat. No. 5,279,575 the trocar has a pair of flukes which are pivotally coupled to the body with pins. The trocar also includes a rigid clamp which is slidably on the outer tube for securing the trocar to a body wall. The inner tube slides longitudinally relative to the outer tube for moving the flukes to the open position. A distal end of the inner tube engages a camming surface on each of the flukes for camming the flukes outward.

The trocar disclosed in U.S. Pat. No. 5,279,575 suffers from a number of drawbacks. First, the clamp is relatively stiff and does not conform to the shape of the patient. As such, the trocar may be difficult to tilt at a desired angle when passing between adjacent ribs. Another drawback of the trocar is that the hinges create a relatively large profile since the hinges extend beyond the outer, cylindrical surface of the tube. The relatively large profile increases trauma to the patient which is particularly problematic when the trocar is rotated or otherwise displaced after initial placement. Yet another drawback of U.S. Pat. No. 5,279,575 is that the clamp is mounted to a third tube which slides over the outer tube. The three tube configuration also increases the profile of the device and trauma to the patient.

SUMMARY OF THE INVENTION

The present invention solves the problems with known trocars by providing a trocar body having arms which lie within a cylinder defined by the trocar body. The arms are positioned within the cylinder when in the closed position so that the profile of the trocar is minimized. The arms are preferably integrally formed with the tubular portion. An actuator is positioned within the body and movable with respect to the body in a longitudinal direction. The actuator slidingly engages the arms for moving the arms from the closed position to the open position. In a preferred embodiment, the actuator is rotatably coupled to the body by a pin and slot configuration. Rotation of the actuator moves the distal end of the actuator longitudinally to engage the arms for moving the arms to the open position.

The trocar also preferably includes a resilient member attached to the body. The resilient member is configured to provide a clamping force on tissue positioned between the arms and the resilient member when the arms are in the closed position. The resilient member provides advantages over conventional clamps since the resilient member conforms to the shape of the patient.

In another aspect of the present invention, a trocar is provided with a deflectable member coupled to the distal end of an outer member. The deflectable member has first and second ends with the first end coupled to an inner member. The inner member is rotatably coupled to the outer member for moving the first end between open and closed positions. When the first end is in the open position the deflectable member is deflected outwardly for locking the trocar to a patient. The first end travels along an arcuate path when moving between the open and closed position. In a preferred embodiment, the inner and outer members are substantially cylindrical and the deflectable member is integrally formed with the outer member.

In yet another aspect of the present invention, a trocar includes an inner member and an outer member surrounding at least a portion of the inner member. The inner member includes arms which are movable between closed and open positions. The arms are configured to lock the trocar to a patient when in the open position. The outer member is attached to the arms for moving the arms to the open position. The outer member is moved longitudinally relative to the inner member to move the arms to the open position.

In another aspect of the present invention, a trocar includes an inner member having arms at a distal end. The arms are biased toward an open position and are restrained in the closed position by an outer member which engages an outer surface of the arms. When the outer member is retracted, the outer member is spaced apart from the outer surface of the arms which permits the arms to move to the open position. In a preferred embodiment, the outer member is substantially cylindrical and slidingly engages the inner member when moving the arms to the closed position.

In yet another aspect of the present invention, a trocar includes arms which have interlocking elements. The interlocking elements hold the arms in a closed position. The interlocking elements are preferably hooks which are deflected to disengage from one another when an instrument is inserted through the trocar. The arms are naturally biased toward the open position so that the arms move to the open position when the hooks disengage.

In another aspect of the present invention, a trocar is provided which includes a deflectable member. The deflectable member is movable between first and second positions with both the first and second positions being stable, unbiased positions. The deflectable member preferably has a frustoconical shape which is angled toward the distal end in the first position and toward the proximal end in the second position. The trocar is inserted into the patient with the deflectable member in the first position to facilitate introduction into the patient. When it is desired to remove the trocar, the trocar is pulled with sufficient force to move the deflectable to the second position for removal of the trocar from the patient.

These and other features will become apparent with the following description of the preferred embodiments.

BRIEF DESCRIPTION OF THE DRAWINGS

FIG. 14 is an isometric view of a fifth trocar with arms in a closed position.

FIG. 15 is an isometric view of a fifth trocar with arms in the open position.

FIG. 16 is a view of the bottom of the fifth trocar.

DESCRIPTION OF THE PREFERRED EMBODIMENTS

Figure 1:
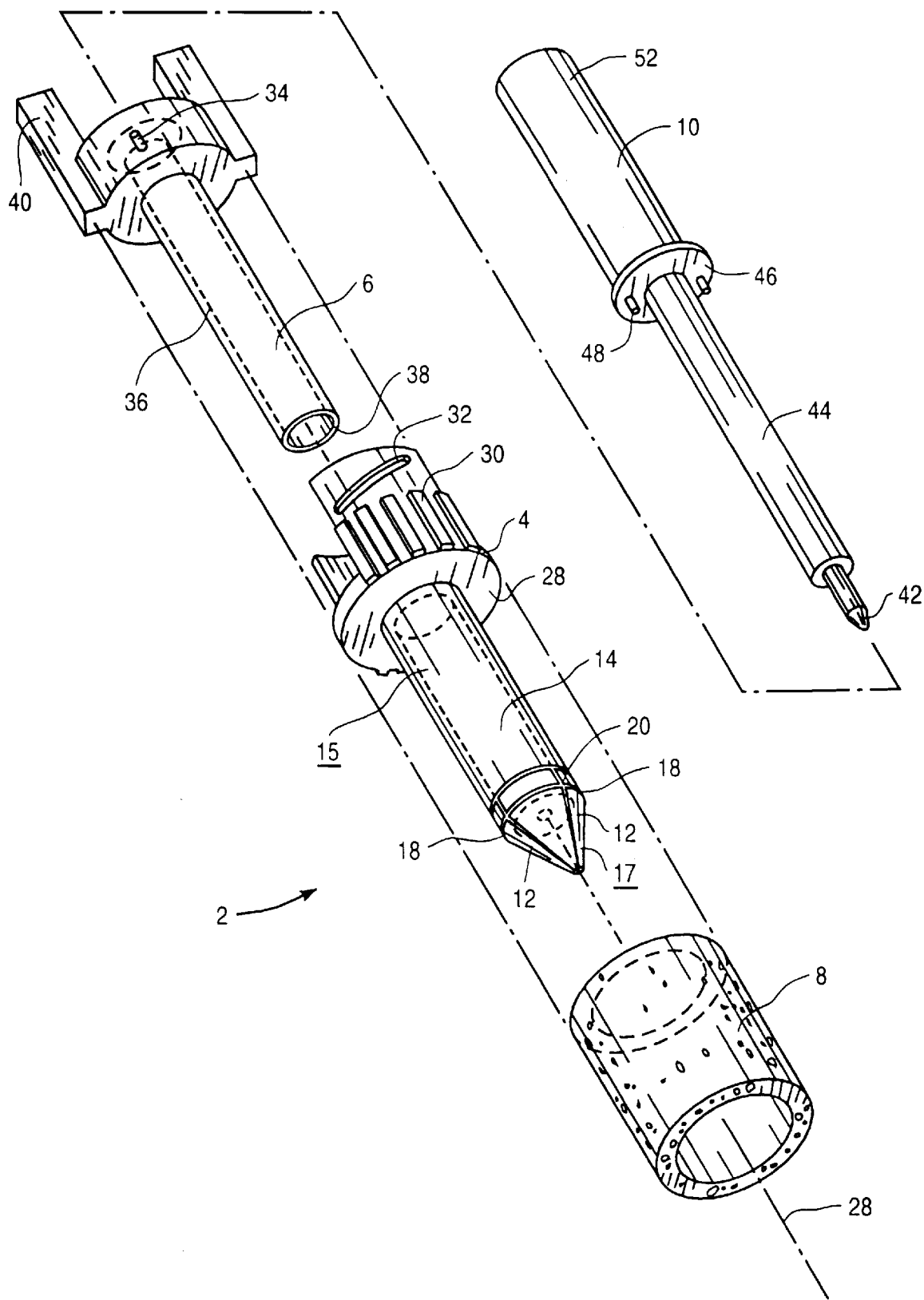
FIG. 1 is an exploded view of a first trocar.

Referring to FIG. 1, a trocar 2 constructed in accordance with the present invention is shown. The trocar 2 includes a body 4, an actuator 6, a resilient member 8, and an obturator 10 which is optional. The body 4 includes a number of arms 12 which are movable from the closed position of FIG. 2 to the open position of FIG. 3. As will be described below, the actuator 6 is used to move the arms 12 from the closed position of FIG. 2 to the open position of FIG. 3.

Figure 2:
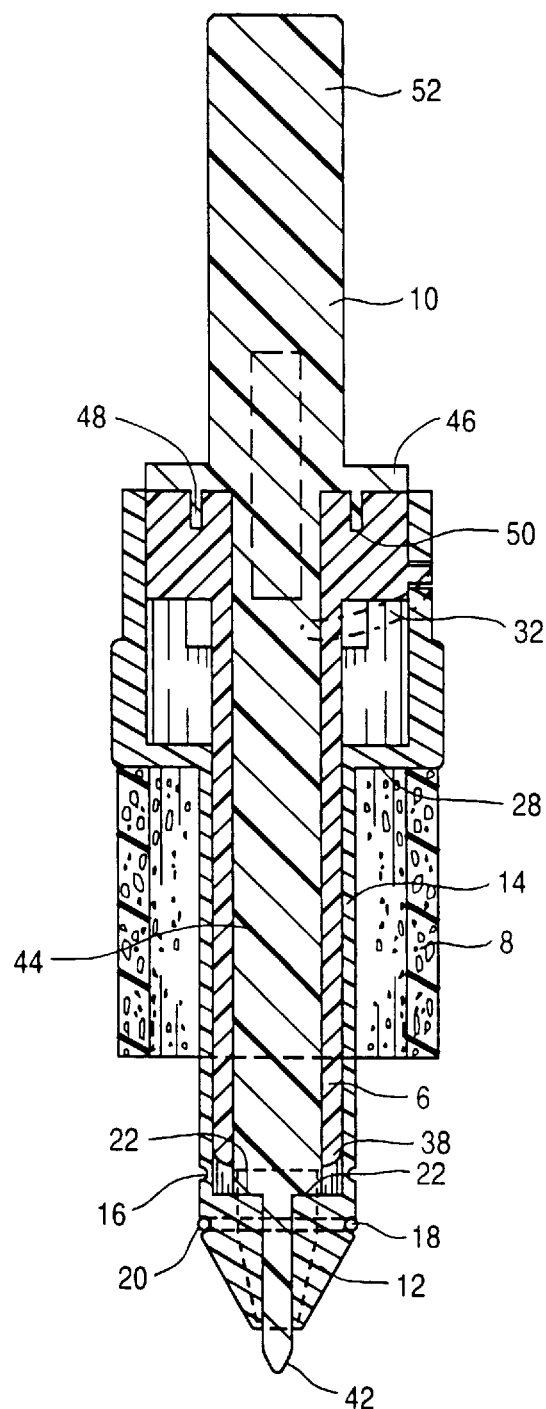
FIG. 2 is a cross-sectional view of the first trocar with arms in a closed position.

Referring now to FIGS. 1 and 2, the body 4 includes a tubular portion 14 having an exterior surface 15 which defines a cylinder. The arms 12 of the present invention advantageously do not extend outside the cylinder defined by the external surface 15 of the tubular portion 14 so that trauma to a patient is minimized. The small profile of the trocar 2 is accomplished by forming the arms 12 integrally with the tubular portion 14.

Figure 3:
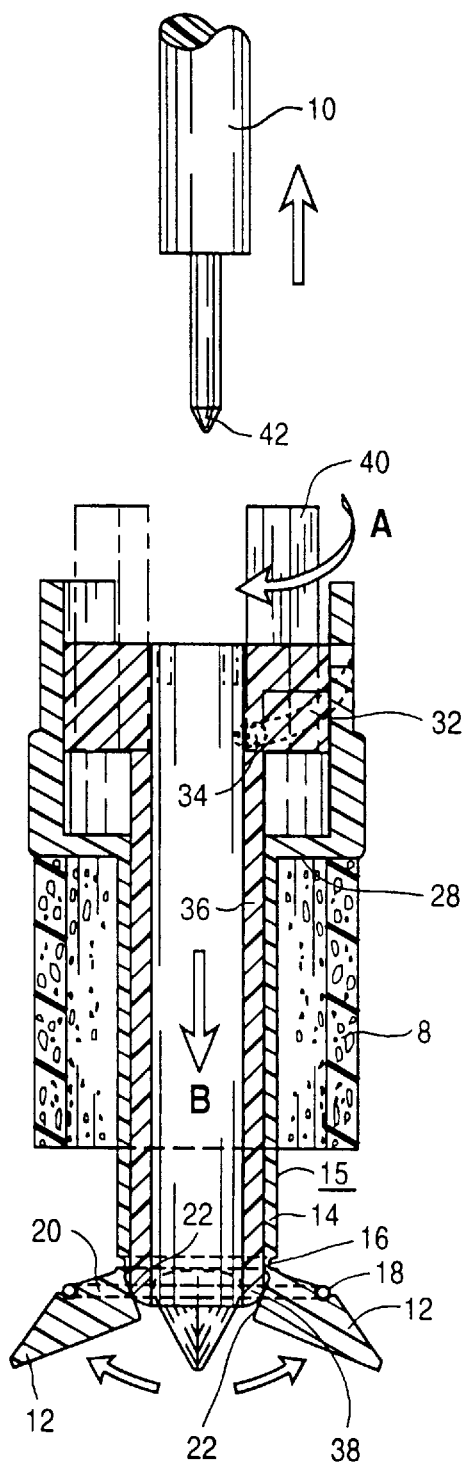
FIG. 3 is a cross-sectional view of the first trocar with the arms in an open position.

The arms 12 preferably form a tip and form an outer surface 17 having a conical or frustoconical shape. A notch 16 is provided where the arms 12 bend when moving from the closed position to the open position. The arms 12 are preferably biased toward the closed position by an o-ring 18 positioned in a groove 20. Referring to FIGS. 2 and 3, the arms 12 each include a slide surface 22 which is engaged by the actuator 6 when moving the arms 12 from the closed position to the open position. The slide surface 22 is oriented substantially perpendicular to a longitudinal axis 26, however, the slide surface 22 may also have any other orientation including curved to facilitate deflection of the arms 12 from the closed position to the open position. The arms 12 are moved from the closed position to the open position by the actuator 6 as will be described below.

A flange 28 is connected to the proximal end of the tubular portion 14. The flange 28 includes ribs 30 and an arcuate slot 32. The slot 32 receives a pin 34 attached to the actuator 6. The pin 34 and slot 32 configuration produces a longitudinal displacement of the actuator 6 relative to the arms 12 when the actuator 6 is rotated relative to the body 4.

The actuator 6 includes a member 36, which is preferably a cylindrical tube, having a distal end 38 which contacts and engages the slide surface 22 for moving the arms 12 to the open position. The actuator 6 also includes a pair of extensions 40 which are grasped by the user for rotating the actuator 6 relative to the body 4.

The resilient member 8 is preferably cylindrical with an annular cross-sectional shape. A preferred material for the resilient member 8 is polyurethane foam although any resilient material may be used. The resilient member 8 is preferably spaced apart from the tubular portion 14 which facilitates angling the trocar 2 when the trocar 2 is positioned between adjacent ribs. The space between the resilient member 8 and tubular portion 14 permits radial deflections of the resilient member 8 to facilitate angling of the trocar 2. The resilient member 8 is preferably attached to the flange 28 with an adhesive. Another advantage of the resilient member 8 is that it conforms to the patient thereby reducing trauma to the patient. A further advantage of the resilient member 8 is that it does not require manipulation of set screws and the like as is required with the trocar of U.S. Pat. No. 5,279,575.

Referring to FIG. 2, the obturator 10, which is optional, has a tip 42 which extends beyond the distal tip of the arms 12. Alternatively, the obturator 10 may be omitted with the arms 12 forming the tip as shown in FIG. 1. The tip 42 of the obturator 10 is preferably rounded to reduce trauma to the patient when the trocar 2 is inserted into the patient. The obturator 10 includes a shaft 44 and a flange 46 having a pair of pins 48 which engage holes 50 in the actuator 6. The proximal end has a handle 52 for manipulating the obturator 10. The obturator 10 may also be used to rotate the actuator 6 by rotating the handle with the pins 48 engaging the holes 50 in the actuator 6.

Use of the trocar 2 is now described with reference to FIGS. 2 and 3. Referring to FIG. 2, the arms 12 are shown in the closed position. The o-ring 18 biases the arms 12 toward the closed position. When using the trocar 2 to access the thoracic cavity, a hole is formed between adjacent ribs in the patient and the trocar 2 is inserted into the hole with the arms 12 in the closed position. Referring to FIG. 3, the actuator 6 is then rotated in the direction of arrow A. The pin 34 engages the slot 32 and moves the actuator 6 longitudinally in the direction of arrow B. The distal end of the actuator 6 engages the slide surface 22 thereby deflecting the arms 12 to the open position. With the obturator 10 removed, the throughhole may be used for the introduction of surgical instruments into the patient's thoracic cavity. When the trocar 2 is used in the thoracic cavity, the arms 12 engage the thoracic wall and the resilient member 8 engages the patient's chest. The resilient member 8 is compressed thereby providing a clamping action on the body cavity wall between the resilient member 8 and the arms 12 to anchor the trocar 2. The clamping action secures the trocar 2 to the body wall and minimizes the length of the trocar 2 extending beyond the body wall and into the patient.

Figure 5:
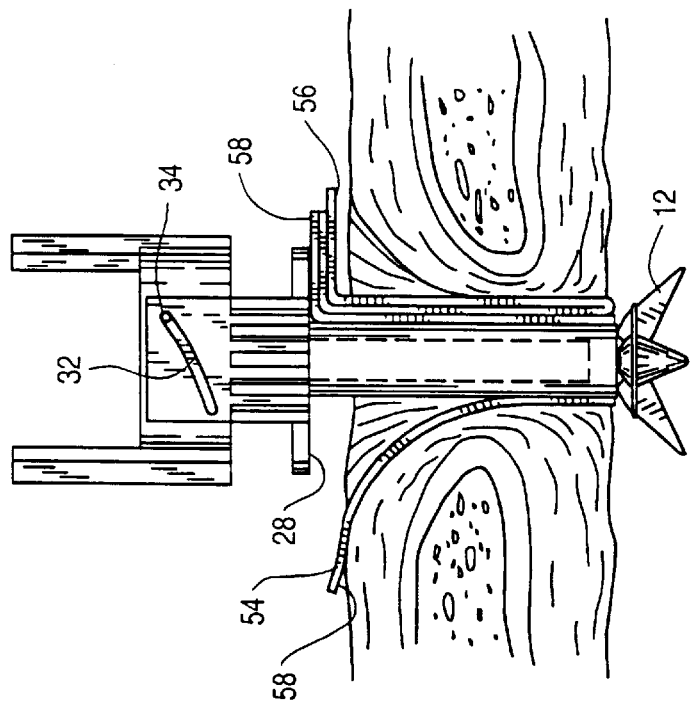
FIG. 5 is a side view of the second trocar with an adhesive strip adhering the second trocar to the patient.
Figure 4:
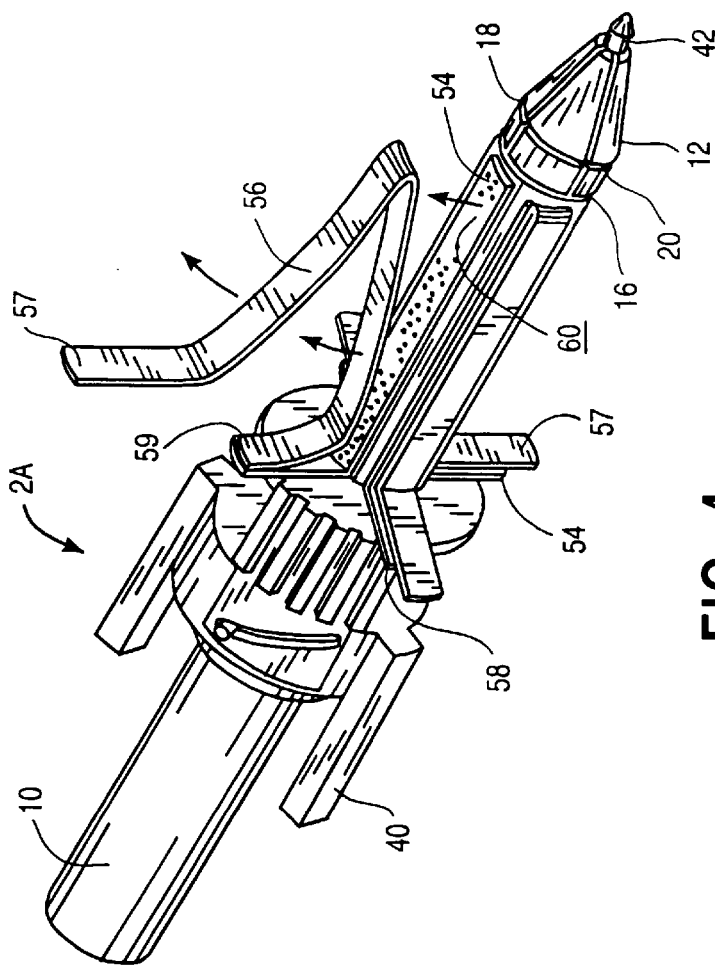
FIG. 4 is an isometric view of a second trocar.

Referring to FIGS. 4 and 5, a second trocar 2A is shown. The trocar 2A is the same as trocar 2 with the exception that the resilient member 8 is replaced by a number of adhesive strips 54 with like reference numerals referring to like structure. The adhesive strips 54 are used to anchor the trocar 2A to the patient. An advantage of the adhesive strips 54 is that when the trocar 2A is angled with respect to the outer surface of the patient, the adhesive strips 54 may be used in the appropriate location to maintain the angular orientation.

A removable cover 56 covers each of the adhesive strips 54. The cover 56 has a pull tab 57 extending outwardly from the flange 28. The cover 56 doubles back upon itself so that an end 59 of the cover 56 is also positioned near the flange 28. The cover 56 may, of course, be simply a strip of material which terminates at the distal end or which has a perforated end which tears away from the body 4. After the cover 56 has been removed, a tab 58 on the adhesive strip 54 is pulled so that the adhesive strip 54 tears away from the body 4. An adhesive side 60 is then adhered to the patient's skin. Referring to FIG. 5, the arms 12 are in the open position to engage an inner thoracic wall. If the trocar 2A is removed from the patient, the adhesive strip 54 is preferably torn away completely from the body 4. If the trocar 2A is inserted into the patient again, another one of the adhesive strips 54 is used to secure the trocar 2A to the patient.

Figure 7:
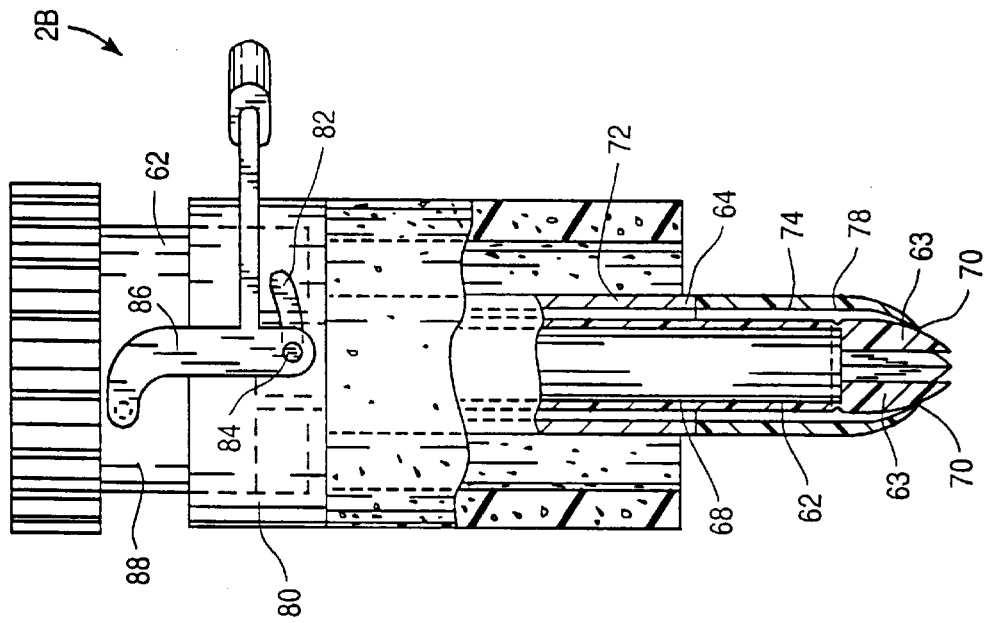
FIG. 7 is a cross-sectional view of the third trocar with arms in a closed position.
Figure 6:
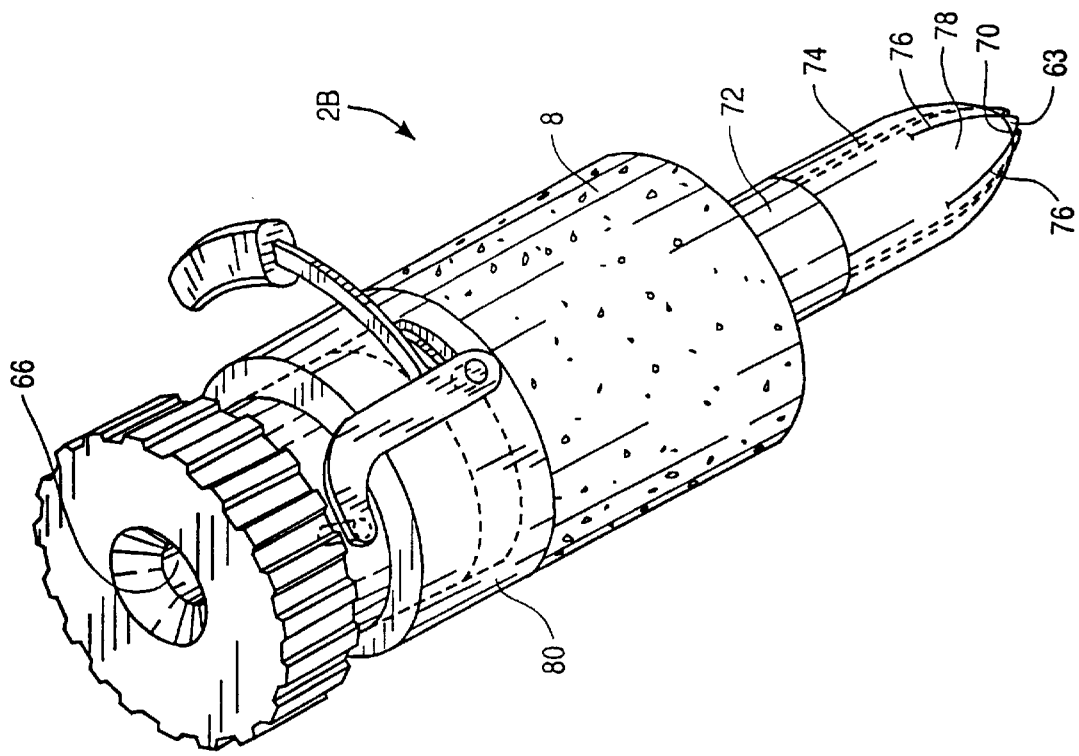
FIG. 6 is an isometric view of a third trocar.

Referring to FIGS. 6 and 7, a third preferred trocar 2B is shown. The trocar 2B includes an inner member 62 which extends through an outer member 64. The inner member 62 includes a throughhole 66 for introduction of medical instruments into a patient.

A number of arms 63 are integrally formed with a tubular portion 68 of the inner member 62. Although it is preferred that the arms 63 are integrally formed with the tubular portion 68, the arms 63 may also be pivotally coupled to the tubular portion 68 with a pinned connection. The arms 63 are naturally biased toward the closed position of FIG. 6, however, the trocar 2B may also include the groove and o-ring of FIG. 1 and 2.

The outer member 64 has a distal end 70 which is coupled to the arms 63. The outer member 64 has a rigid cylindrical portion 72 and an elastomeric portion 74 which has the distal end 70 attached to the arms 63. The distal end 70 of the outer member 64 has a number of slots 76 therein which form a number of sections 78 corresponding to the arms 63 with each of the sections 78 being connected to one of the arms 63.

The outer member 64 is rigidly coupled to a ring 80 and a resilient member 8 is attached to the ring 80. The resilient member 8 is preferably the same as the resilient member 8 described above in connection with FIGS. 1 and 2. The ring 80 includes a curved slot 82 which receives a pin 84 attached to a lever 86. The other end of the lever 86 is pinned to an extension 88 of the inner member 62.

Figure 9:
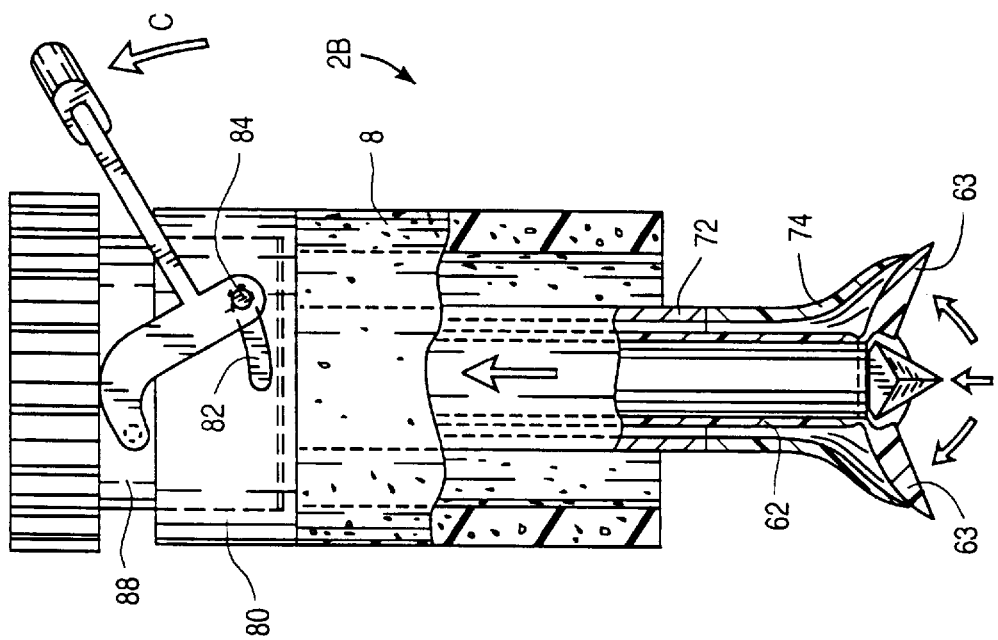
FIG. 9 is a cross-sectional view of the third trocar with the arm in a closed position.
Figure 8:
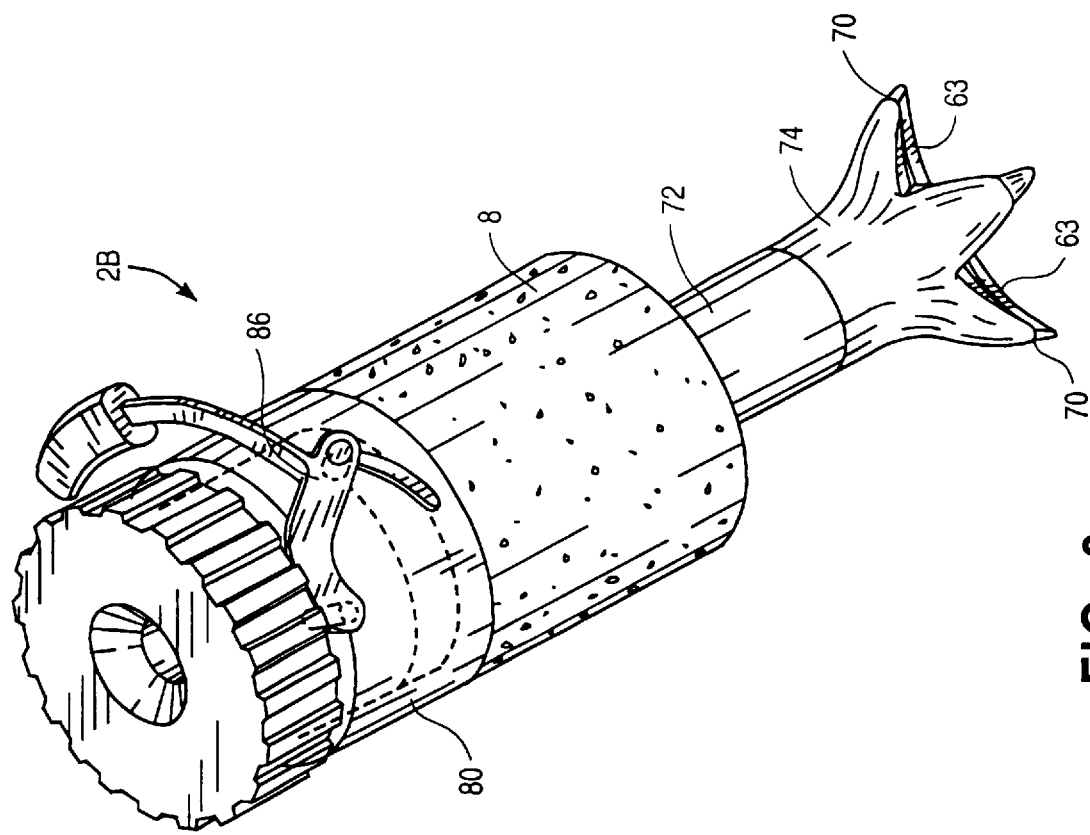
FIG. 8 is an isometric view of the third trocar with the arms in an open position.

Referring to FIGS. 8 and 9, pivoting of the lever 86 in the direction of arrow C moves the inner member 62 longitudinally relative to the outer member 64. The relative motion causes the outer member 64 to go into tension so that the outer member pulls the arms 63 to the open position of FIGS. 8 and 9. Although it is preferred to use the lever 86 to produce relative longitudinal displacement between the inner and outer members 62, 64, the inner and outer members 62, 64 may also be simply slidable relative to one another or have the pin and slot configuration of FIGS. 1 and 2.

Figure 11:
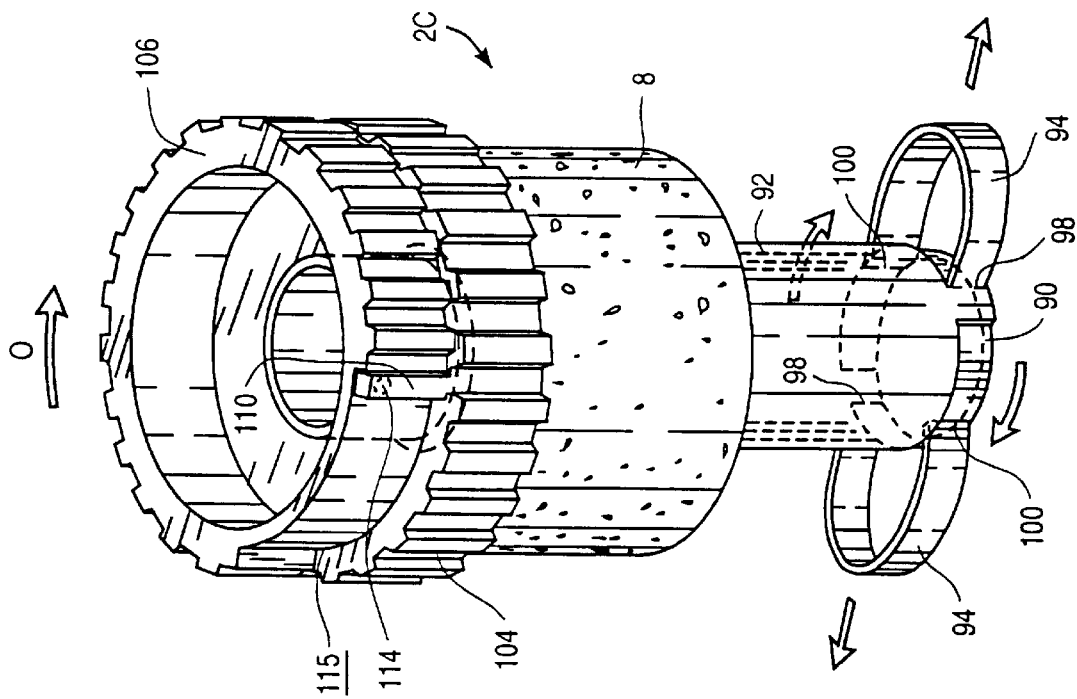
FIG. 11 is an isometric view of the fourth trocar with the arms in a closed position.
Figure 10:
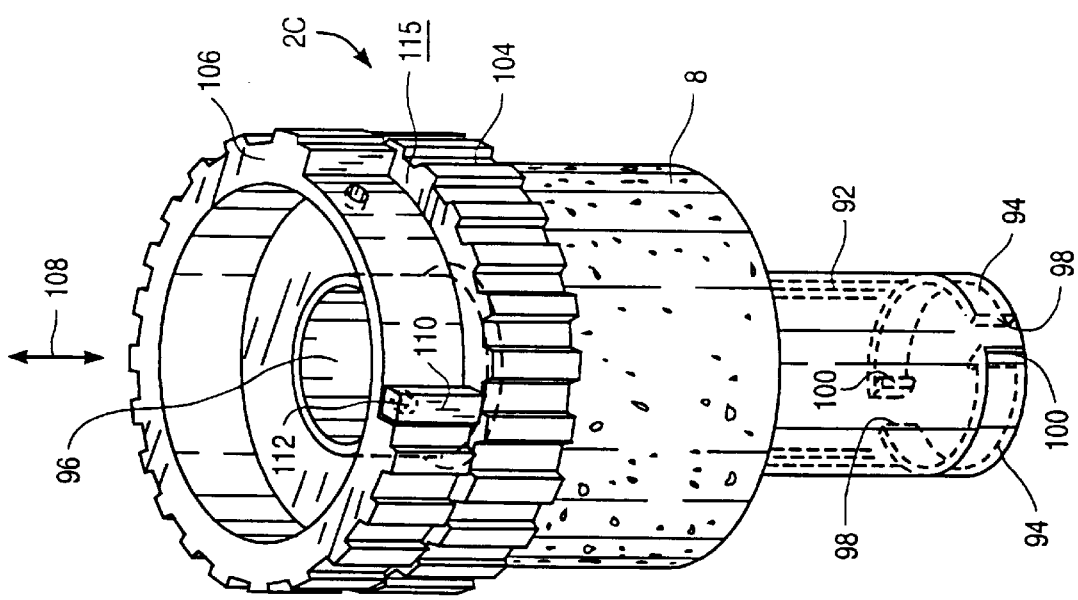
FIG. 10 is an isometric view of a fourth trocar with arms in an open position.

Referring to FIGS. 10 and 11, a fourth preferred trocar 2C is shown. The trocar 2C includes an inner member 90 rotatably coupled to an outer member 92. Arms 94 are mounted to the outer member. The arms 94 are movable from the closed position of FIG. 10 to the open position of FIG. 11. As will be described below, the arms 94 are moved from the closed position to the open position by relative rotational motion between the inner and outer members 90, 92. The inner and outer members 90, 92 may take any shape, however, a preferred shape is cylindrical. A through hole 96 extends through the trocar 2C for the introduction of surgical instruments.

The arms 94 are preferably formed by making two L-shaped cuts in the distal end of the outer member 92. The arms 94 each include a first end 98, which is coupled to the outer member 92, and a second end 100, which is attached to the inner member 90. The first end 98 is preferably integrally formed with the outer member 92. The outer member 92 is coupled to a ring 104 and a resilient member 8 is attached to the ring 104. The resilient member 8 is preferably the same as described above and serves the same purpose. Although it is preferred to use the resilient member 8, a conventional clamp may be also be used such as the clamp disclosed in U.S. Pat. No. 5,279,575

The inner member 90 is coupled to a driver 106. When the driver 106 is rotated in the direction of arrow D the second end 100 travels along an arcuate path toward the first end 98. The arcuate path preferably lies in a plane which is substantially perpendicular to a longitudinal axis 108 of the inner member 90. The arcuate path may be oriented in any other configuration relative to the longitudinal axis 108 and preferably forms an angle of between 90° and 45° with the longitudinal axis 108.

Figure 13:
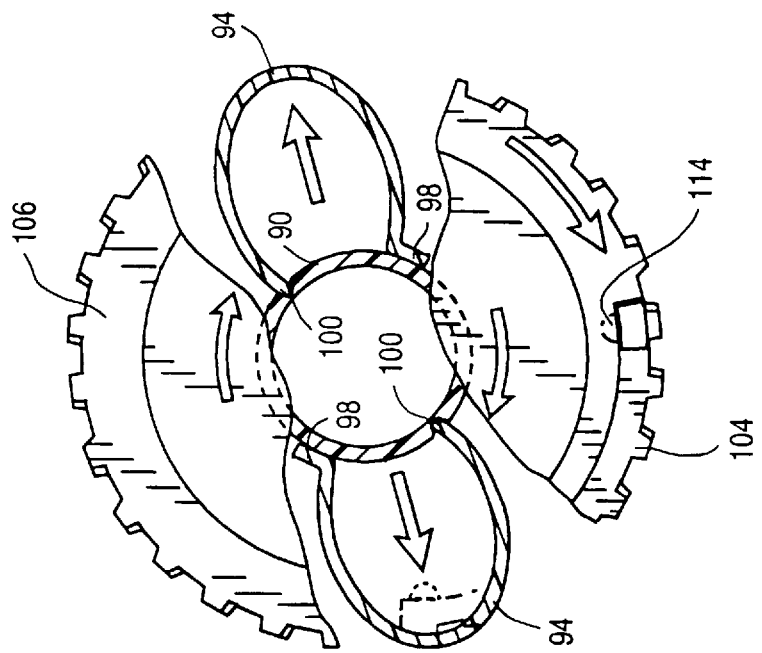
FIG. 13 is another partial cut-away plan view of the fourth trocar with the arms in the open position.
Figure 12:
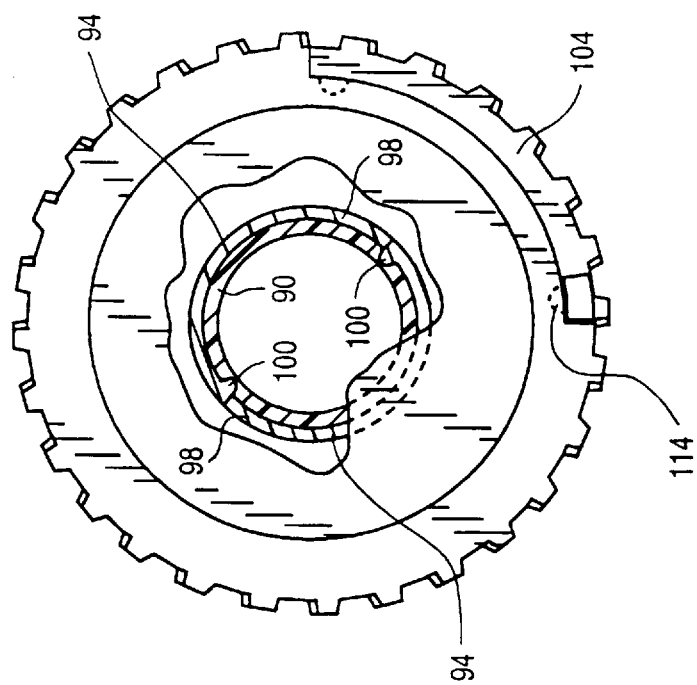
FIG. 12 is a partial cut-away plan view of the fourth trocar with the arms in the closed position.

FIGS. 12 and 13 are partial cut-aways showing the arms 94 in the closed and open positions, respectively. Although it is preferred to provide two arms 94, any number of arms 94 may be provided. The arms 94 are preferably both positioned at the same longitudinal position, however, the arms 94 may also be positioned at different locations along the longitudinal axis. Furthermore, the arms 94 may include a hinge between the first and second ends 98, 100 to form a predetermined shape.

The inner and outer members 90, 92 may be locked in the open and closed positions. Referring to FIG. 10 and 11, an extension 110 extends from the ring 104. The extension 110 has a protrusion 112 which is configured to engage detents 114 in the driver 106. The driver 106 includes a cut-out 115 in which the extension 110 is positioned. The actuator 6 is locked and unlocked by twisting the driver 106 with a sufficient force to deflect the extension 110 so that the protrusion 112 engages or disengages from the detent 114.

Referring to FIGS. 14–16, a fifth trocar 2D is shown. The trocar 2D includes a number of arms 116 which have interlocking elements 118 which, in the preferred embodiment, are hooks. Referring to the end view of FIG. 16, the interlocking elements 118 engage one another to retain the arms 116 in the closed position of FIG. 14. The arms 116 are naturally biased toward the open position of FIG. 15 and the interlocking elements 118 retain the arms 116 in the closed position of FIG. 14. The arms 116 are preferably integrally formed with a tubular portion 120. The trocar 2D includes a through hole 122 for introduction of surgical devices into the patient.

Referring to FIG. 15, the arms 116 include slide surfaces 124. The interlocking elements 118 are disengaged from one another by inserting an instrument into the throughhole 122 to engage the slide surfaces 124. The instrument deflects the interlocking elements 118 until they become disengaged from one another. After the interlocking elements 118 are disengaged, the arms 116 move to their natural, unbiased, position of FIG. 15. The trocar 2D also includes the resilient member 8, however, a conventional clamp may also be used. Although it is preferred to use hooks as the interlocking elements 118, the interlocking elements 118 may have any other structure. For example, the interlocking elements 118 may be an adhesive or a frangible connection which could be machined or formed by melting the arms 116 together and which is broken by the instrument. Alternatively, the connection may be melted or broken by a heated instrument. Furthermore, although it is preferred that the interlocking elements 118 be disengaged with any medical instrument, a specialized opener may be used which engages the arms 116. The specialized instrument could include teeth which engage teeth on the arms 116 so that a rotational action is used to disengage the interlocking elements 118. The specialized instrument may also be used to hold the arms in the closed position and is simply removed to permit the arms to move to the unbiased, open position.

Figure 18:
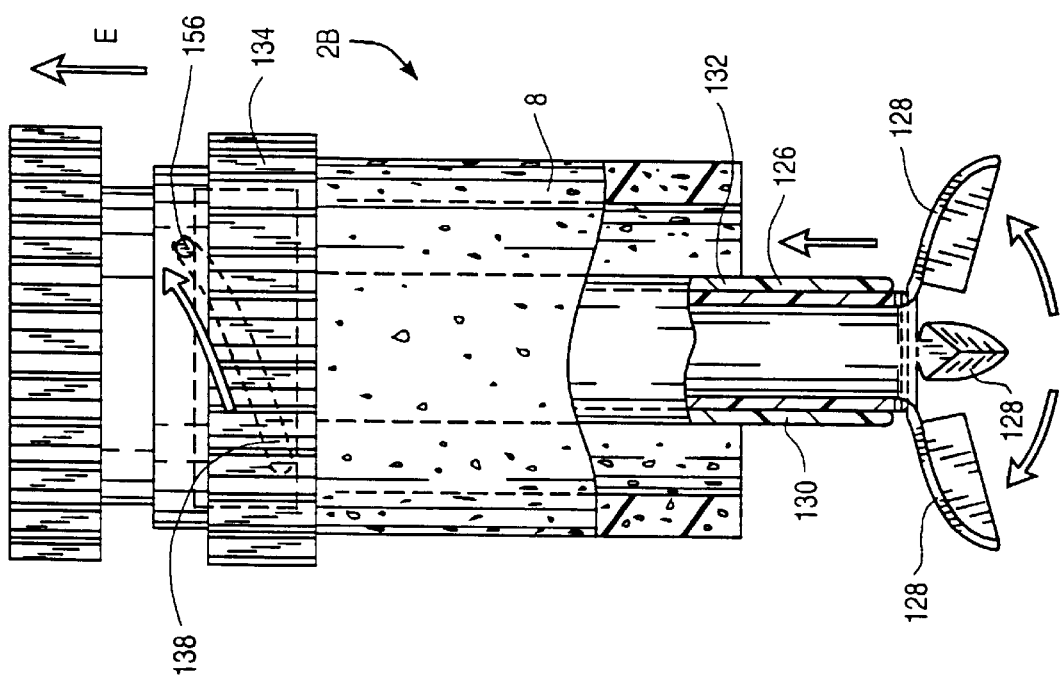
FIG. 18 is a partial cross-sectional view of the sixth trocar of FIG. 17.
Figure 17:
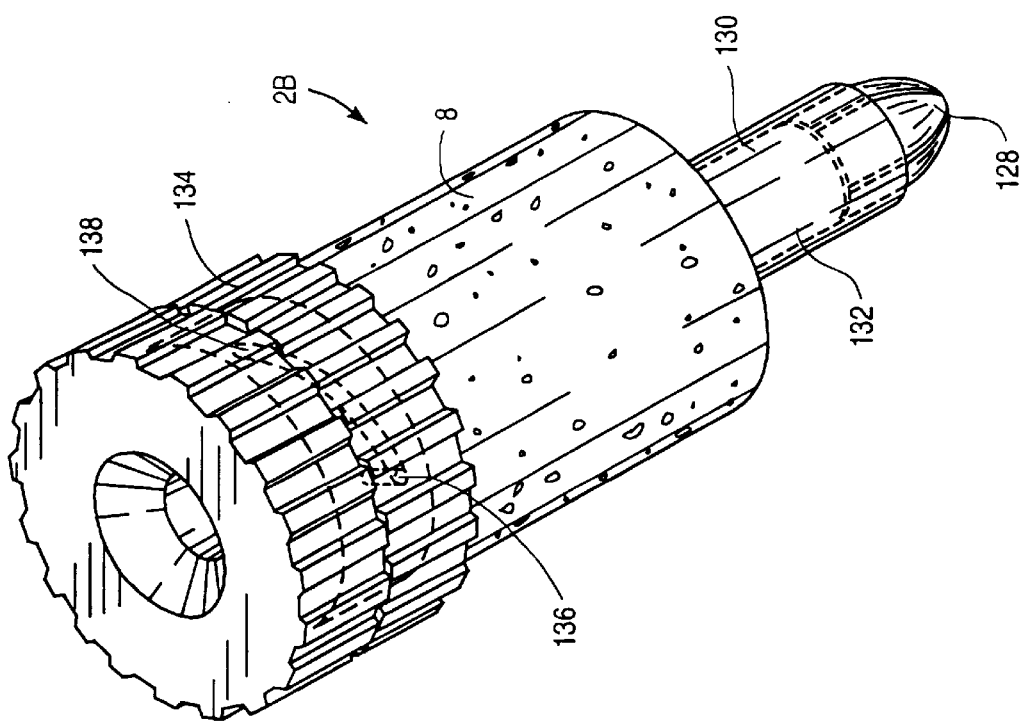
FIG. 17 is an isometric view of a sixth trocar.

Referring to FIGS. 17 and 18, a sixth preferred trocar is shown. The trocar 2E includes an inner member 126 having a number of arms 128 at a distal end 130. The arms 128 are naturally biased to the open position of FIG. 18 and are maintained in the closed position of FIG. 17 by an outer member 130. The outer member 130 has a cylindrical portion 132 connected to a disc 134. The trocar 2E preferably includes the resilient member 8, however, a conventional clamp may also be used.

The inner member 126 includes a pin 136 which engages a slot 138 in the outer member 130. Rotation of the disc 124 causes the outer member 130 to displace longitudinally in the direction of arrow E. The distal end of the outer member 130, which restrains the arms 128 in the closed position of FIG. 17, is spaced from the arms 128 thereby permitting the arms 128 to move to the unbiased, open position of FIG. 18. The arms 128 are preferably integrally formed with the inner member 126 and are preferably made of a polyolefin plastic although any suitable material may be used. To remove the trocar 2E, the disc 134 is rotated so that the distal end of the outer member 130 forces the arms 128 to the closed position of FIG. 10. The trocar 2E is then removed from the patient. Alternatively, the trocar 2E may be simply pulled from the patient with the body wall deflecting the arms 128 inward as they pass through the body wall.

Figure 19:
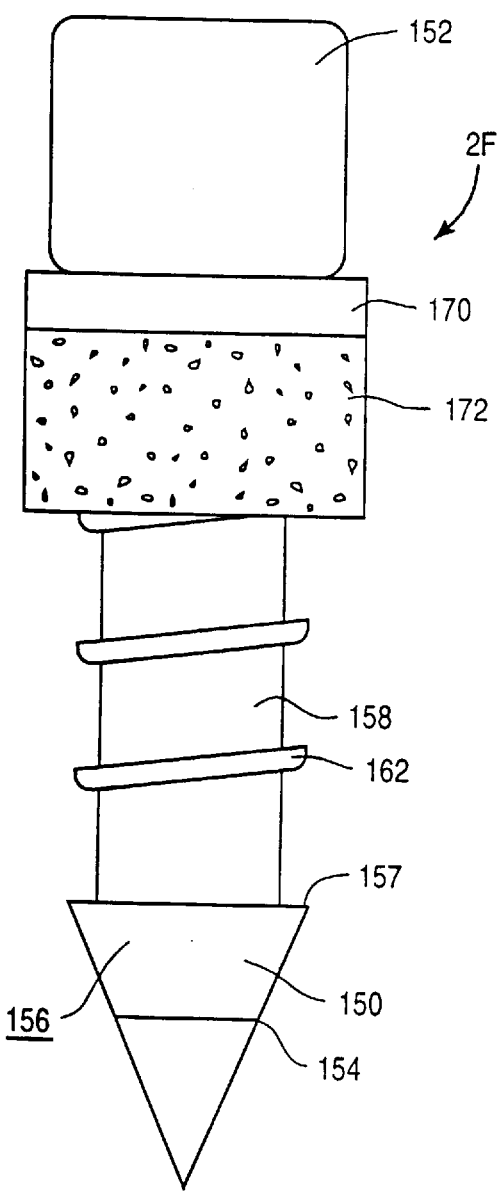
FIG. 19 is a side view of a seventh trocar.

Referring to FIG. 19, a seventh trocar 2F is shown which includes a deflectable member 150. An obturator 152 extends through the trocar 2F beyond a distal end 154 of the trocar 2F. The deflectable member 150 has an outer surface 156 which preferably has a frustoconical shape. The deflectable member 150 also has an inner surface which is spaced apart from the wall so that the deflectable member 150 may be deformed when inserted into the patient.

Figure 21:
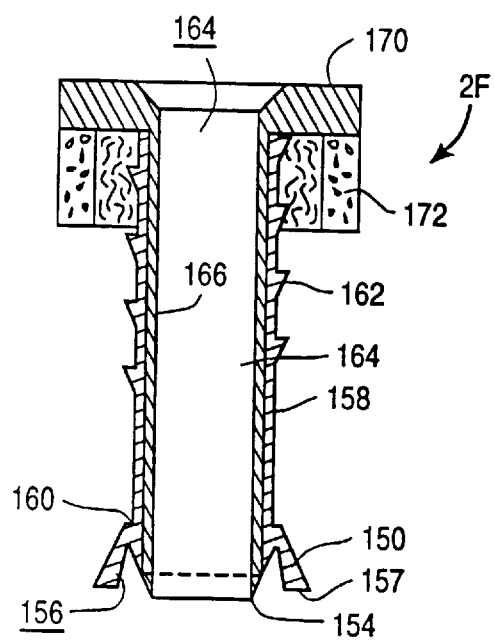
FIG. 21 is a cross-sectional view of the seventh trocar with the deflectable member in a second position.

The deflectable member 150 is shown in a first position in FIG. 19 with the outer surface 156 being angled toward the distal end 154. Referring to the cross-sectional view of FIG. 21, the deflectable member 150 is shown in the second position in which the outer surface 156 is angled toward the proximal end. The outer surface 156 and inner surface of the deflectable member 150 are everted when moving from the first position to the second position. The deflectable member 156 preferably moves from the first position to the second position upon application of an axial force of between 2 and 5 lbs and more preferably between 3 and 4 lbs.

Figure 20:
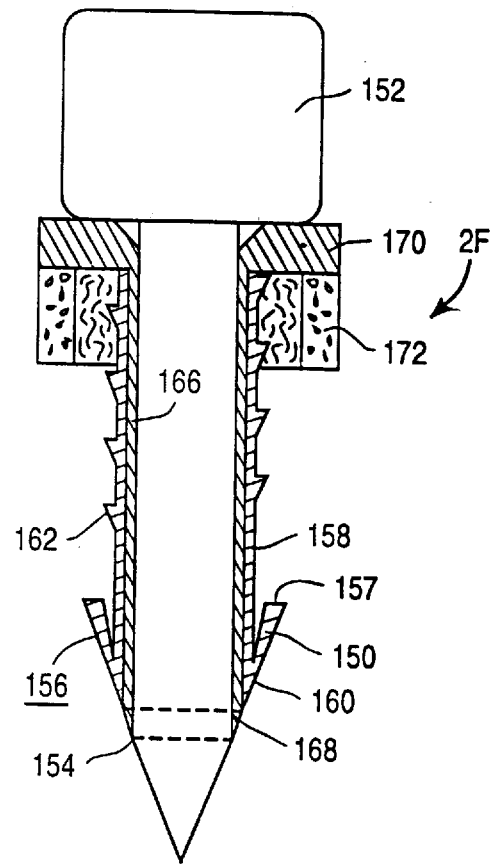
FIG. 20 is a cross-sectional view of the seventh trocar with a deflectable member in a first position.

Referring to FIG. 20, the deflectable member 150 is integrally formed with an elastomeric sheath 158. The sheath 158 is made of silicone rubber however, any other suitable elastic material may be used. The deflectable member 150 has a hinge 160 which is stable in both the first position of FIG. 20 and the second position of FIG. 21. The deflectable member 150 has a free end 157 which is positioned proximal of the hinge 160 when the deflectable member 150 is in the first position and which is distal to the hinge 160 when the deflectable member 150 is in the second position. The sheath 158 includes a helical thread 162 so that the user may also rotate the trocar 2F to position the trocar 2F in the chest wall or other body structure. The thread 162 also helps prevent inadvertent removal of the trocar 2F. The trocar 2F may, of course, be formed without the helical thread 162 or with circumferential ribs if desired. An instrument delivery lumen 164 passes through the trocar 2F for introducing surgical instruments into a patient. The instrument delivery lumen 164 may also include gas seals if a gas, such as carbon dioxide, is introduced and retained into the patient.

The sheath 158 is mounted to an inner cannula 166 which is made of a low friction plastic so that surgical instruments pass easily through the instrument delivery lumen 164 without binding. The sheath 158 may either be attached to the inner cannula 166 with an interference fit or with an adhesive. The inner cannula 166 and sheath 158 could also be coninjection molded to provide a single cannula with the sheath 158 being an elastomer and the inner cannula 156 being a low friction plastic. A distal end of the inner cannula 166 has a beveled edge 168 and extends beyond the sheath 158. The beveled edge 168 provides a smooth transition between the obturator 152 and trocar 2F. The beveled edge 168 also provides a smooth transition between the inner cannula 166 and deflectable member 150.

The inner cannula 166 has a flange 170 at the proximal end. A clamp 172 is mounted to the bottom of the flange 170 to provide a clamping force on a body structure positioned between the clamp 172 and the deflectable member 150. The clamp is also used to retract the distal end of the trocar 2F so that the deflectable member 150 engages a body structure such as the thoracic wall. The clamp 172 is preferably the same as the resilient member 8 described above in connection with FIGS. 1–3, however, any other clamp may be used such as a coil spring.

The above description merely describes the preferred embodiments and it is understood that variations of the preferred embodiment are within the scope of the invention which is defined by the claims. For example, the trocar 2D may include the outer member 130 to move the arms 12 to the closed position after the interlocking members 118 have been disengaged, and the obturator 10 may be used with any of the trocars described herein.

What is claimed is:

1. A device used for introducing a surgical instrument into a patient, comprising:
    a body having a proximal end and a distal end;
    an instrument delivery lumen extending through the body; and
    a deflectable member coupled to the body and being made of an elastomeric material, the deflectable member having an outer surface which is angled toward the distal end of the body when the deflectable member is in a first, unbiased position, the deflectable member also having a free end and an attachment end which is coupled to the body, the free end extending around the instrument delivery lumen and being spaced apart from the body when the deflectable member is in the first position, the deflectable member being deflectable from the first position to a second position, the free end being positioned nearer the proximal end than the attachment end when in the first position and being positioned further from the proximal end than the attachment end when in the second position, the deflectable member having an inner surface opposite the outer surface, the inner and outer surfaces having a frustoconical shape.

2. The device of claim 1, wherein:
    the second position is a stable, unbiased position.

3. The device of claim 2, wherein:
    the outer surface of the deflectable member extends around the instrument delivery lumen.

4. The device of claim 1, wherein:
the deflectable member is configured to deflect from the first position to the second position upon application of a force between 2 and 5 lbs.

5. The device of claim 1, wherein:
the body includes a helical thread on an exterior surface.

6. The device of claim 1, further comprising:
a removable obturator extending through the instrument delivery lumen and beyond the distal end of the body.

7. The device of claim 1, further comprising:
a clamp coupled to the body, the clamp being configured to clamp a body structure between the deflectable member and the clamp.

8. The device of claim 1, wherein:
the outer surface is angled toward the proximal end when the deflectable member is in the second position.

9. A device used for introducing a surgical instrument into a patient, comprising:
a body having a proximal end and a distal end;
an instrument delivery lumen extending through the body; and
a deflectable member coupled to the body and being made of an elastomeric material, the deflectable member having an outer surface which is angled toward the distal end of the body when the deflectable member is in a first, unbiased position, the deflectable member also having a free end and an attachment end which is coupled to the body, the free end extending around the instrument delivery lumen and being spaced apart from the body when the deflectable member is in the first position, the deflectable member being deflectable from the first position to a second position, the free end being positioned nearer the proximal end than the attachment end when in the first position and being positioned further from the proximal end than the attachment end when in the second position;
the body including an elastomeric sheath;
the deflectable member being integrally formed with the elastomeric sheath.

10. A method of providing an instrument delivery path into a patient comprising the steps of:
providing a trocar including a body having a deflectable member and an instrument delivery lumen, the deflectable member being movable between a first position and a second position, the first position being a stable unbiased position, the deflectable member being movable from the first position to the second position upon application of a deflecting force to the deflectable member, the deflectable member having a free end and an attachment end, the attachment end being coupled to the body and the free end being spaced apart from the body, the free end being positioned closer to the proximal end than the attachment end when the deflectable member is in the first position and the free end being positioned further from the proximal end than the attachment end when the deflectable member is in the second position;
inserting the trocar into the patient thereby forming an opening in the patient the deflectable member being in the first position after being inserted into the patient so that withdrawal of the trocar is resisted by the free end contacting the patient;
introducing an instrument into the patient through the instrument delivery lumen;
removing the instrument from the instrument delivery lumen; and
removing the trocar from the patient after the instrument removing step, the trocar removing step being carried out so that the free end engages the patient and the deflecting force is exerted on the deflectable member to move the deflectable member from the first position toward the second position.

11. The method of claim 10, further comprising the step of:
positioning an obturator in the instrument delivery lumen before the inserting step; and
removing the obturator before the introducing step.

12. The method of claim 10, wherein:
the trocar removing step being carried out so that the deflecting force is between 2 to 5 lbs to move the deflectable member to the second position.

13. The method of claim 10, further comprising the step of:
clamping a body structure between the deflectable member and a clamp which is coupled to the body.

* * * * *